United States Patent [19]
Katsuura et al.

[11] Patent Number: 6,008,403
[45] Date of Patent: Dec. 28, 1999

[54] METHOD FOR PRODUCING OPTICALLY ACTIVE AMINO ACID OF DERIVATIVE THEREOF HAVING HIGH OPTICAL PURITY

[75] Inventors: Kimio Katsuura, Tokyo; Shigeaki Irino, Yamaguchi, both of Japan; Akira Tokuda, Sittard, Netherlands

[73] Assignee: Tosoh Corporation, Yamaguchi, Japan

[21] Appl. No.: 08/938,670

[22] Filed: Sep. 26, 1997

[30] Foreign Application Priority Data

| Sep. 27, 1996 | [JP] | Japan | ................................... 8-256153 |
| Sep. 27, 1996 | [JP] | Japan | ................................... 8-256154 |
| Sep. 27, 1996 | [JP] | Japan | ................................... 8-256155 |

[51] Int. Cl.$^6$ .......................... C07C 229/00; C07B 57/00
[52] U.S. Cl. ........................... 560/40; 560/170; 562/401; 562/402; 260/471
[58] Field of Search ................... 560/40, 170; 562/401, 562/402; 260/471; 195/29

[56] References Cited

U.S. PATENT DOCUMENTS

| 3,878,043 | 4/1975 | Matta et al. | ................................ 195/29 |
| 4,533,506 | 8/1985 | Lahav et al. | ............................. 260/501 |
| 4,847,409 | 7/1989 | Kidman et al. | ......................... 562/401 |
| 4,864,031 | 9/1989 | Zbaida et al. | ........................... 548/344 |
| 5,248,813 | 9/1993 | Manimaran et al. | .................... 562/401 |

*Primary Examiner*—Gary Geist
*Assistant Examiner*—Taylor V. Oh
*Attorney, Agent, or Firm*—Howrey & Simon; Jeffrey I Auerbach

[57] ABSTRACT

A method for producing an optically active amino acid or derivative thereof having a high optical purity from an optically active amino acid comprising optical isomers or derivative thereof, which comprises any one of processes (A), (B), and (C), wherein the process (A) comprises the steps: (1) previously preparing an optically active amino acid or derivative thereof having an optical purity higher than a convergent value of a mutual solubility of the optical isomers and (2) crystallizing the optically active amino acid or the derivative thereof that exists in excess, said convergent value being a ratio of the desired optical isomer in the optical isomers dissolved in a mother liquor in which crystals of a racemate and an optically active compound coexist at equilibrium (the optical purity in a mother liquor). The processes (B) and (C) are described in the specification.

17 Claims, No Drawings

METHOD FOR PRODUCING OPTICALLY ACTIVE AMINO ACID OF DERIVATIVE THEREOF HAVING HIGH OPTICAL PURITY

FIELD OF THE INVENTION

This invention relates to a process for producing an optically active amino acid or amino acid derivative having a high optical purity. Optically active amino acids, especially L-compounds, are of extreme importance as nutrient sources for animals. D-Compounds have been recently increasing their value has raw materials of medicines. Similarly, optically active amino acid esters are useful as raw materials of medicines, assistants in asymmetric syntheses or raw materials of ligands of catalysts.

BACKGROUND OF THE INVENTION

There are several methods available for optical resolution of racemic amino acids or racemic amino acid esters. For example, methods known for optical resolution of DL-phenylalanine or an alkyl ester thereof include (1) crystallization into a phenylalanine methylsulfate (see JP-A-6-306029 (the term "JP-A" as used herein means an "unexamined published Japanese patent application")), (2) use of a resolving reagent, such as an N-acylamino acid (see JP-B-51-17522 (the term "JP-B" as used herein means an "examined Japanese patent publication"), U.S. Pat. No. 3,941,831) or a dipeptide derivative (see JP-B-62-56857), (3) use of an enzyme, such as an acylase for resolution of an N-acylamino acid (see U.S. Pat. No. 3,907,638) or a protease for resolution of an amino acid ester (see U.S. Pat. Nos. 3,813,317 and 3,878,043), and (4) acid decomposition of an adduct of a dipeptide derivative and a D-amino acid ester (see JP-B-59-43159).

Each of these methods produces an optical isomer having a relatively high optical purity through relatively easy operations. However, it has been difficult to recover an optically active amino acid or amino acid derivative having a high optical purity of 99% or higher.

In particular, the above-described method for producing an optically active amino acid ester is disadvantageous in that the workability is poor due to poor filterability of the adduct; when the adduct contains impurities, such as an L-amino acid ester and a DL-amino acid, the purification efficiency is poor; and the operation of filtration is tedious for industrial production and requires expensive equipment.

JP-B-2-12238 and JP-B-2-12240 disclose a method in which an adduct of a dipeptide derivative (which is enzymatically produced from an N-substituted-α-amino acid and a DL-amino acid ester) and a D-amino acid ester is recovered as a slurry in a water-immiscible organic solvent, and the adduct is decomposed with an acid to recover a D-amino acid ester. According to this method, however, the unreacted DL-amino acid ester and a DL-amino acid as a decomposition product are simultaneously recovered, making it impossible to recover a D-amino acid or derivative thereof at an optical purity of 99% or higher.

In these days, optically active amino acids or derivatives thereof that have been increasing in importance for use as raw materials of medicines are required to have a high optical purity as well as a high chemical purity from the standpoint of efficacy and side effects. It has been keenly demanded therefore to develop a method for producing an optically active amino acid or derivative thereof having a high optical purity through simple and easy operations with high industrial productivity.

SUMMARY OF THE INVENTION

An object of the present invention is to provide a less costly and more efficient method for producing an optically active amino acid or derivative thereof having such a high optical purity that the desired optical isomer (D-compound) is present in a ratio of 99/1 or higher.

As a result of extensive studies, the inventors of the present invention have found that optical isomers of an amino acid or derivative thereof dissolved in a solution have the following characteristic of mutual solubility. That is, there is a specific composition area or condition in which the optically active amino acid or derivative thereof as dissolved in a solution has a constant optical purity (hereinafter referred to as a "convergent value") irrespective of the optical purity of the crystal introduced. In other words, in crystallizing the optically active amino acid or derivative thereof, where the solubility ratio of the optical isomers in a mother liquor before crystallization is higher than the convergent value, it is possible to crystallize one of the optical isomers that is present in excess preferentially. In this case, however much the optical isomer crystallizes out of the mother liquor, the equilibrium concentration does not change, and crystallization continues to yield a desired optically active amino acid or derivative thereof efficiently. Conversely, where the solubility ratio of the optical isomers in a mother liquor is lower than the equilibrium concentration, the optical purity of the precipitating crystals is lower than the convergent value.

Accordingly, the present invention provides a method for producing an optically active amino acid or derivative thereof having a high optical purity from an optically active amino acid or derivative thereof (inclusive of a hydrochloride) comprising optical isomers, which comprises the following steps:

(1) previously preparing an optically active amino acid or derivative thereof having an optical purity higher than a convergent value of a mutual solubility of the optical isomers, and (2) crystallizing the optically active amino acid or derivative thereof that exists in excess, said convergent value being a ratio of the desired optical isomer in the optical isomers dissolved in a mother liquor in which crystals of a racemate and an optically active compound coexist at equilibrium (the optical purity in a mother liquor), and said ratio being constant irrespective of the ratio of the crystals of the racemate and the optically active compound (hereinafter referred to as "process (A)").

Furthermore, where the above-mentioned specific composition area or condition, in which a dissolved amino acid or derivative thereof has an optical purity of the convergent value, is established, and where the solvent is water or a mixed solvent of water and a water-soluble solvent, the inventors have found that the dissolved amino acid or derivative thereof has an inherent optical purity depending on the pH region.

Based on this finding, the present invention provides a method for producing an optically active amino acid or derivative thereof having a high optical purity from an optically active amino acid or derivative thereof (inclusive of a hydrochloride) comprising optical isomers, which comprises the following steps:

(1) crystallizing an optically active compound at a pH around its isoelectric point, and (2) lowering the pH of the mother liquor from which the resulting crystals have been collected to 1 or less, followed by crystallization (hereinafter referred to as "process (B)").

Moreover, the present invention provides a method for producing an optically active amino acid or derivative thereof having a high optical purity from an optically active amino acid or derivative thereof (inclusive of a hydrochloride) comprising optical isomers, which comprises the following steps:

(1) reacting an optically active amino acid ester comprising optical isomers with an N-substituted-α-L-aspartyl-L-phenylalanine alkyl ester represented by the following formula (I):

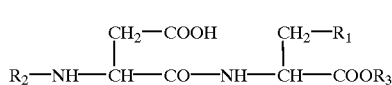

(I)

wherein $R_1$ represents a substituted or unsubstituted phenyl group; $R_2$ represents an aliphatic oxycarbonyl group or a substituted or unsubstituted benzyloxycarbonyl group; and $R_3$ represents an alkyl group, by mixing in an aqueous solution to form an adduct of the N-substituted-α-L-aspartyl-L-phenylalanine alkyl ester and the D-amino acid ester, (2) extracting the resulting adduct with a water-immiscible organic solvent to separate the adduct in the form of an organic solvent slurry from an aqueous phase, (3) purifying the organic-solvent slurry containing the adduct by washing with an acid aqueous solution, and (4) subjecting the organic solvent slurry to acid decomposition with an acid aqueous solution to recover the D-amino acid ester having a high optical purity as an acidic aqueous solution (hereinafter referred to as "process (C)").

The above optically active amino acids and derivatives thereof can have an optical purity of 99% or higher.

DETAILED DESCRIPTION OF THE INVENTION

The amino acids which are applicable to crystallization according to the present invention and parent amino acids from which the amino acid derivatives applicable to crystallization are derived are represented by the following formula (II):

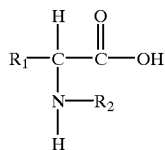

(II)

wherein $R_1$ represents a straight-chain or branched alkyl group, an alkylthio group, an alkoxy group, a benzyl group or an indolalkyl group, each of which may be substituted with a hydroxyl group, a halogen atom, an alkyl group or a nitro group; $R_2$ represents a straight-chain or branched alkyl group, a benzyl group, an alkylcarbonyl group, an alkoxycarbonyl group, an arylcarbonyl group or an arylalkylcarbonyl group, each of which may be substituted with a hydroxyl group, a halogen atom, or a nitro group; and $R_1$ and $R_2$ may be combined with each other to form a ring.

Examples of the amino acids represented by formula (II) are valine, alanine, leucine, isoleucine, methionine, phenylglycine, phenylalanine, naphthylalanine, tyrosine, tryptophan, homophenylalanine, 3,4-dihydroxyphenylalanine, 2,4-dihydroxyphenylalanine, 3,4-methylenedioxyphenylalanine, 3,4-dimethoxyphenylalanine, 3(4)-methoxy-4(3)-hydroxyphenylalanine, 3,4-isopropylidenedioxyphenylalanine, proline, piperidinecarboxylic acid, and pyrazinecarboxylic acid.

It is generally desirable for the amino acid of formula (II) subjected to crystallization to have as high an optical purity as possible, which means an increase in the amount of a desired optically active compound that could be recovered. To have a high optical purity for the amino acid is not always desirable because, in some cases, such cannot be achieved without a laborious pretreatment.

The optically active amino acid comprising optical isomers represented by formula (II), which is to be crystallized according to the present invention, can be prepared with ease in a conventional manner, such as optical resolution of a racemic compound or asymmetric synthesis starting from a prochiral precursor. A racemate obtained by partial racemization of a fermentation liquid resulting in a fermentation method for preparing an amino acid is also useful.

The amino acid derivatives derived from the amino acid represented by formula (II) are represented by the following formula (III):

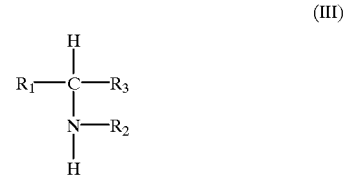

(III)

wherein $R_1$ and $R_2$ are the same as defined above; and $R_3$ represents any functional group derived from the carboxyl group of formula (II), such as a straight-chain or branched alkyl group different from $R_1$, an ester group derived from a substituted or unsubstituted straight-chain or branched aliphatic compound or a substituted or unsubstituted aromatic compound, an amido group derived from a primary or secondary aliphatic or aromatic amine, a methylol group, an alkoxymethylol group or a thioester group.

The amino acid derivatives represented by formula (III) typically include esters represented by the following formula (IV):

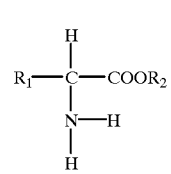

(IV)

wherein $R_1$ represents a straight-chain or branched alkyl group, an alkylthio group, an alkoxy group, a benzyl group or an indolalkyl group, each of which may be substituted with a hydroxyl group, a halogen atom, an alkyl group or a nitro group; and $R_2$ represents a straight-chain or branched alkyl group different from $R_1$.

Examples of the esters (IV) include alkyl esters of valine, alanine, leucine, isoleucine, methionine, phenylglycine, phenylalanine, naphthylalanine, tyrosine, tryptophan, homophenylalanine, 3,4-dihydroxyphenylalanine, 2,4-dihydroxyphenylalanine, 3,4-methylenedioxyphenylalanine, 3,4-dimethoxyphenylalanine, 3(4)-methoxy-4(3)-hydroxyphenylalanine, 3,4-isopropylidenedioxyphenylalanine, proline, piperidinecarboxylic acid or pyrazinecarboxylic acid.

The alcoholic residue of the ester moiety preferably includes a methoxy group and an ethoxy group.

The amino acids represented by formula (II) or derivatives thereof represented by formulae (III) and (IV) preferably include phenylglycine which may be substituted at its phenyl ring, and derivatives thereof; phenylalanine which may be substituted at its phenyl ring, and derivatives thereof; homophenylalanine, derivatives which may be substituted at its phenyl ring, and derivatives thereof; and naphthylalanine which may be substituted at its naphthyl ring, and derivatives thereof.

In carrying out crystallization under prescribed conditions according to the present invention, it is preferred to use the amino acid derivatives having good crystallizing properties. In this connection, the amino acid represented by formula (II) can be in the form of a mineral acid salt, such as a hydrochloride or a sulfate, or an alkali metal or alkaline earth metal salt, such as a sodium salt, a potassium salt or a calcium salt. The amino acid salt can be isolated by subjecting an aqueous solution of the product as purified by crystallization to ion-exchange treatment with an ion-exchange resin or precipitation by neutralization.

The amino acids and the derivatives thereof represented by formulae (II) to (IV) which are to be crystallized by process (A) must have an optical purity higher than the convergent value of the mutual solubility between their optical isomers. It is generally but not always desirable that the amino acid or derivative thereof present in the mother liquor before crystallization should have as high an optical purity as possible, increasing the amount of a desired optically active compound that could be recovered. To have a high optical purity for the amino acids and the derivatives thereof is not always desirable when such involves a laborious pretreatment.

The optically active compounds of the amino acids and the derivatives thereof comprising the optical isomers represented by formulae (II) to (IV), which are to be crystallized, can be prepared with ease in a conventional manner, such as optical resolution of a racemic compound or asymmetric synthesis starting from a prochiral precursor. A racemate obtained by partial racemization of a fermentation liquid resulting in a fermentation method for preparing an amino acid is also useful.

In carrying out crystallization under prescribed conditions according to the present invention, it is preferred to use the amino acid derivatives having good crystallizing properties. In this connection, the amino acids and the derivatives thereof represented by formulae (II) to (IV) can be in the form of a mineral acid salt, such as a hydrochloride or a sulfate. The amino acid of formula (II) can also be in the form of an alkali metal or alkaline earth metal salt, such as a sodium salt, a potassium salt or a calcium salt. The amino acid salt can be isolated by subjecting an aqueous solution of the product as purified by crystallization to ion-exchange treatment with an ion-exchange resin or precipitation by neutralization.

Depending on the kind, the amino acids and the derivatives thereof can take a plurality of crystal forms or can be amorphous. For example, phenylalanine takes an α-form or a β-form. In the present invention, the crystal form in the crystallization process is not particularly limited.

While it is desirable that the crystallization according to the present invention be carried out in an aqueous solution to avoid an organic solvent's remaining in the final product, a mixed solvent of water and a water-miscible organic solvent can be used with no problem. Useful water-miscible organic solvents include alcohols, such as methanol, ethanol and propanol; ketones, such as acetone, methyl ethyl ketone; ethers, such as tetrahydrofuran and dioxane; carboxylic acids, such as formic acid and acetic acid; and nitrites, such as acetonitrile. Organic solvents in which the optically active amino acid or derivative thereof is soluble can be employed.

The water-containing solution for crystallization may contain an organic or inorganic salt. The presence of the salt is rather preferred in some cases from the standpoint of the crystallization efficiency and the crystal form of a precipitating amino acid or amino acid ester hydrochloride, etc. Useful salts include alkali metal salts, e.g., sodium chloride and potassium chloride, alkaline earth metal salts, e.g., magnesium chloride and calcium chloride, and amine salts, e.g., ammonium chloride.

A preferred salt content of the solution is subject to variation depending on the solubility of the salt and the amino acid or derivative thereof in the aqueous medium but is usually 30% by weight or lower based on the weight of the mother liquor before crystallization. At salt concentrations higher than 30%, the salt tends to enter the collected crystals, bringing about little further improvement of the above-described effects.

Crystallization is carried out by ordinary techniques, such as neutralization, concentration, and cooling. Producing a larger difference in solubility and resulting in a higher recovery efficiency, crystallization by neutralization is preferred for an amino acid. While not limiting, crystallization by cooling is preferred for an amino acid ester hydrochloride. Crystals can also be obtained by mixing an aqueous solution of an amino acid or derivative thereof with a water-miscible organic solvent showing little or no dissolving power for the amino acid or derivative thereof.

The pH adjustment for crystallization can be performed by any method as long as the amino acids and the derivatives thereof represented by formulae (II) to (IV) remain soluble in the mother liquor and maintains its structure stably. Acids or bases for the pH adjustment is not particularly limited. Preferred acids include mineral acids, such as hydrochloric acid and sulfuric acid, and preferred bases include sodium hydroxide and potassium hydroxide.

The concentration of the amino acid or derivative thereof solution subjected to crystallization is not particularly specified because their solubility is largely affected by the content of a salt if any, the pH, the kind of solvent and, in using a mixed solvent, the mixing ratio of solvents.

Where process (A) is followed, the mutual solubility of optical isomers of an amino acid or derivative thereof is determined beforehand to obtain the above-identified convergent value, from which various conditions of crystallization can be decided.

When both crystals of a racemate and an optically active compound coexist in a mother liquor at equilibrium, the dissolved optically active compound in which one of the optical isomers that is to be recovered is present in excess has a constant optical purity (convergent value) irrespective of the ratio of the crystals of the optically active compound to the racemate, i.e., the optical purity of the crystals. Accordingly, when a mother liquor contains an amino acid or derivative thereof having an optical purity higher than the convergent value, the composition of the mother liquor is adjusted by, for example, concentration so that the solubility of the unnecessary other optical isomer reaches saturation, whereby only the desired optical isomer is selectively crystallized. The convergent sometimes varies depending on the kind of the amino acid or derivative thereof and the conditions of crystallization. With respect to a pH condition of a mother liquor, in particular, there is a specific pH range in which an amino acid or derivative thereof has an intrinsic convergent value.

After crystallization, the mother liquor from which the precipitated crystals have been separated by, for example, filtration contains the amino acid or derivative thereof having an optical purity of the convergent value. Therefore, the mother liquor can be recovered and treated to increase the optical purity higher over the convergent value by optical resolution or a like technique and then reused as a mother liquor for crystallization.

While not limiting, the crystallizing temperature is 60° C. or lower because the solubility becomes lower to increase the rate of crystallization at lower temperatures.

Since the collected crystals sometimes contain impurities originating from the mother liquor, etc., they can be washed with an appropriate solvent, if desired.

While process (A) makes it feasible to collect crystals having an optical purity of 99% or higher, crystals having a lower optical purity may be collected, if desired.

Where process (B) is followed, crystallization is carried out in two stages of different pH regions in which different convergent values are observed. The pH region in which an amino acid or derivative thereof shows a higher convergent value (i.e., an amino acid compound dissolved in a mother liquor at equilibrium with crystals of an optically active compound comprising crystals of a desired optical isomer has a higher optical purity) is, for example, in the vicinity of the isoelectric point of the amino acid solution subjected to crystallization, in which region general crystallization by neutralization is conducted. Such a pH range can be from 4 to 8. For example, the pH range for this stage of crystallization of phenylalanine is preferably 5 to 6.

After the first stage crystallization, the precipitated crystals of the optically active compound having a high optical purity are collected by filtration, etc. The mother liquor is then subjected to second stage crystallization in the pH region showing a lower convergent value to further recover the optically active compound.

The pH region for the second stage crystallization is 1 or less, preferably 0.3 to 1.0. At a pH exceeding 1, a sufficient difference cannot be made in equilibrium concentration. At a pH lower than 0.3, the solubility becomes extremely higher, resulting in poor efficiency of recovery.

While not restricting, crystallization in this stage is preferably carried out by concentration for ease of operation. The mother liquor from which the crystals of the optically active compound have been collected by, for example, filtration is subjected to crystallization by neutralization, which can be performed in the same manner as the above-described crystallization by neutralization. The neutralization results in precipitation of mixed crystals of the racemate and the optically active compound. It follows that the optical purity of the optically active compound remaining dissolved in the mother liquor increases to its convergent value. The mother liquor is again subjected to crystallization at a pH of 1 or less, preferably 0.3 to 1, to collect the optically active compound in the same manner as the above-described crystallization at a pH of 1 or less.

It is preferred to repeat the above-mentioned two stages of crystallization whereby substantially the whole amount of the excess optical isomer can be recovered from the optically active compound. The number of times of repetition is not particularly limited. It would be decided taking into consideration the cost incurred and the commercial value of the product.

Crystallization according to process (B) may start from the stage of the pH region in which a lower convergent value is exhibited, followed by repetition of the above-described operations.

While process (B) makes it feasible to collect crystals having an optical purity of 99% or higher, crystals having a lower optical purity may be collected, if desired.

While not limiting, the crystallizing temperature in process (B) is 60° C. or lower because the solubility becomes lower to increase the rate of crystallization at lower temperatures.

Since the collected crystals sometimes contain impurities originating from the mother liquor, etc., they can be washed with an appropriate solvent, if desired.

Where process (C) is followed, an amino acid ester represented by formula (IV) is used as a starting material. The amino acid ester (IV) can be either a racemate or an optically active compound provided that it contains a D-amino acid ester. Accordingly, the starting amino acid esters include those having insufficient optical purity which are prepared by optical resolution of a racemate or asymmetric syntheses from prochiral precursors and those obtained by partially racemizing a fermentation product in the treatment of a fermentation liquid.

The amino acid ester (IV) may contain the corresponding amino acid as an impurity. A permissible amino acid content is not particularly limited but is preferably not more than 20% by weight based on the amino acid ester. The amino acid ester can be in a salt form as well as a free amine form. Salts with inorganic acids, e.g., hydrochloric acid, hydrobromic acid and a sulfuric acid, and salts with organic acids, e.g., alkylsulfonic acids and benzoic acid, can be used.

The resolving reagent which can be used in process (C) is a dipeptide represented by formula (I), which is made up of L-aspartic acid having a substituent on its nitrogen atom and an L-phenylalanine ester which may have a substituent on its nucleus. The dipeptide can be used either as a free acid (as represented by formula (I)) or as a salt, such as a salt with an alkaline earth metal, e.g., lithium, sodium, potassium or calcium, or a salt with an amine, e.g., ammonia or dimethylamine.

Addition reaction between the amino acid ester (IV) and the dipeptide resolving reagent (I) is carried out in a solution. As a result, a 1:1 adduct of the dipeptide and the D-amino acid ester is formed or precipitated preferentially or predominantly thereby to accomplish optical resolution into the L-amino acid ester and the D-amino acid ester. The dipeptide resolving reagent is used in an amount of 1 mol or less per mole of the D-amino acid ester contained in the starting amino acid ester.

The solvent for the addition reaction is not limited as far as the dipeptide (I) and the amino acid ester (IV) are soluble therein. Water is a preferred solvent. The aqueous solution may contain a water-miscible organic solvent.

While not limiting, the reaction temperature can range from room temperature to about 60° C.

The reaction solution is preferably kept at a pH of 4 to 8, still preferably from about 5 to about 7. A buffer can be added for the pH maintenance.

The adduct is separated by extraction with a water-immiscible organic solvent to obtain a slurry of the crystals of the adduct. The amount of the water-immiscible organic solvent to be used is not limited, usually ranging from about 0.5 to 5 kg per mole of the adduct.

Examples of suitable extracting solvents include nonpolar solvents, such as n-hexane, benzene, and diethyl ether, esters, such as isobutyl acetate and isopropyl acetate, and ketones, such as methyl isobutyl ketone, with methyl isobutyl ketone and isobutyl acetate being particularly preferred.

While not limiting, the extracting temperature can range from room temperature to about 60° C. The reaction temperature could be the extracting temperature. It is possible to form the adduct by dissolving either one of the compound (I) and the compound (IV) in a water-immiscible organic solvent, dissolving the other in an aqueous solvent, mixing the two solutions, and adjusting the pH in the aqueous solvent. The water-immiscible organic solvent used for dissolving one of the reactants and the extracting solvent may be the same. In this case, the adduct formed is extracted into the organic phase, and separation of the aqueous phase yields the organic solvent slurry of the adduct.

Since the separated aqueous phase contains the unreacted amino acid ester, especially the excess L-amino acid ester, it can be made use of as a raw material for production of a high purity L-amino acid ester.

The crude adduct in the organic solvent slurry is washed with water and a hydrochloric acid aqueous solution. Washing is conducted by adding a washing liquid to the slurry, mechanically stirring the mixture at a prescribed temperature for a prescribed time, allowing the mixture to stand for liquid-liquid separation, and removing the aqueous phase. The stirring is preferably performed vigorously, for example, at a speed of 50 to 400 rpm. The stirring time, while not limited, is from 10 to 30 minutes.

Washing with water is chiefly to remove amino acids present as an impurity. Therefore, the amount of water to be used and the number of times of washing depend on the amino acid content of the slurry. A preferred amount of water is 10 to 200% by weight based on the weight of the organic solvent slurry. The number of times of washing is not limited.

In general, it is difficult to effectively remove an L-amino acid ester present in the organic solvent by washing with water. Besides, amino acids can be removed efficiently by washing with an acid hereinafter described, washing with water is not always essential.

The purpose of washing with an acid aqueous solution is to remove the unreacted amino acid ester, especially the L-amino acid ester. Washing with an acid aqueous solution is accompanied by acid decomposition of part of the adduct, resulting in a reduction in recovery of the D-amino acid ester. Therefore, the acid is preferably used in a total amount of 0.1 to 0.7 mol per mole of the adduct and the unreacted amino acid ester. The washing is preferably carried out at least 2 times. From the viewpoint of operational efficiency, washing is usually repeated 2 to 5 times, while not limiting.

Examples of suitable acids include inorganic Brønsted acids, such as hydrochloric acid, sulfuric acid, and hydrobromic acid, and organic Brønsted acids, such as an alkylsulfonic acid and benzoic acid.

The acid is usually used in a concentration of 0.1 to 5 mol/l, while not limiting.

While not limiting, the washing temperature is preferably room temperature to 60° C. and could be the same as the above-described extracting temperature.

After washing, the organic solvent slurry of the adduct is subjected to acid decomposition to yield the D-amino acid ester of high purity in the form of an acid aqueous solution. The acid decomposition is carried out in the same manner as the above-described washing with an acid aqueous solution. The amount of the acid to be used here is at least an equimole to the adduct to be decomposed, preferably 1.2 to 2.0 molar equivalents.

The D-amino acid ester collected in, e.g., a hydrochloric acid aqueous solution, is adjusted to a prescribed pH, concentrated, and cooled to crystallize into its hydrochloride. If desired, a catalyst may be added to the aqueous phase to conduct hydrolysis, followed by crystallization by neutralization to recover the free D-amino acid.

The separated organic solvent contains the dipeptide (I) useful as a resolving reagent so that it can be made use of for optical resolution of an amino acid ester.

While process (C) has been described with reference only to optical resolution of an amino acid which is effected by use of a dipeptide comprising an N-substituted-L-aspartic acid and an L-phenylalanine alkyl ester as a resolving reagent, process (C) is also applicable to optical resolution of an amino acid using, as a resolving reagent, a dipeptide comprising a different combination of amino acids.

The present invention will now be illustrated in greater detail by way of Examples, but it should be understood that the invention is by no means limited thereto. Process (A):

EXAMPLE 1

Phenylalanine having a varied D/L ratio was dissolved, and the D/L ratio of dissolved phenylalanine was measured.

In 5 ml of pure water was dissolved 0.5 g of NaCl, and 1.0 g of phenylalanine having a D/L ratio of 97/3, 95/5, or 75/25 was suspended therein. The suspension was shaken at 30° C. for 2 hours. The soluble matter was analyzed by high performance liquid chromatography (HPLC) (column: TSK-gel Enantio L1, 4.6 mm (ID)×25 cm, produced by Tosoh Corp.). The results obtained are shown in Table 1.

TABLE 1

| | D/L Ratio | |
|---|---|---|
| Total Phenylalanine | | Soluble Matter |
| 97/3 | | 92.7/7.3 |
| 95/5 | | 93.4/6.6 |
| 75/25 | | 93.3/6.7 |

Irrespective of the optical purity of the phenylalanine introduced, the optical purity of the dissolved phenylalanine was almost constant (D/L ratio=93±1/7±1 corresponding to an optical purity of 92 to 93%). Accordingly, 93% was taken as a convergent value of phenylalanine. In Examples 2 and 3, a solution of a mixture of optical isomers having a greater D/L ratio than the convergent value was subjected to crystallization.

EXAMPLE 2

An aqueous solution (300 g) containing 122.2 mmol of D-phenylalanine and 1.84 mmol of L-phenylalanine (D/L ratio=98.5/1.5) and 300 mmol of HCl was neutralized at 30° C. with a 20% NaOH aqueous solution for crystallization. After cooling to room temperature, the precipitated crystals were collected by filtration by suction, washed with cool water, and dried in vacuo to obtain 97.8 mmol of D-phenylalanine having an optical purity of 99.99% as measured by HPLC. The optical purity of the phenylalanine remaining dissolved in the mother liquor after the crystallization was 92.7%.

COMPARATIVE EXAMPLE 1

The same procedure of Example 2 was repeated, except that 400 g of an aqueous solution having dissolved therein 185.6 mmol of D-phenylalanine having an optical purity of 90.50% and 625 mmol of HCl was neutralized at 30° C. with a 20% NaOH aqueous solution for crystallization. As a result, 109.1 mmol of D-phenylalanine crystals having an optical purity of 88.5% was collected.

EXAMPLE 3

An aqueous solution of 153.2 mmol of D-phenylalanine methyl ester and 4.6 mmol of L-phenylalanine methyl ester (D/L ratio=97.1/2.9) and 335 mmol of HCl in 400 ml of pure water was neutralized to pH 3 with a 20% NaOH aqueous solution and concentrated to a weight of 100 g by means of a rotary evaporator. The concentrate was cooled to about 2° C., and the precipitated crystals were collected by filtration by suction. There was obtained 120.7 mmol of D-phenylalanine methyl ester hydrochloride having an optical purity of 99.97% as measured by HPLC.

EXAMPLE 4

The same procedure as in Comparative Example 1 was repeated, except for using 200 mmol of L-phenylalanine having an optical purity of 95.0%. As a result, 58.4 mmol of L-phenylalanine crystals having an optical purity of 99.9% or higher was collected.

EXAMPLE 5

The convergent value of D-phenylalanine methyl ester hydrochloride was 79.5%. In the following Examples, an aqueous solution of D-phenylalanine methyl ester hydrochloride having an optical value higher than this convergent value was used.

The same procedure as in Example 3 was repeated, except that an aqueous solution of 100 mmol of D-phenylalanine methyl ester hydrochloride having an optical purity of 89.7% was crystallized by cooling at 0 to 2° C. at a pH of around 3. As a result, 45.6 mmol of D-phenylalanine methyl ester hydrochloride having an optical purity of 99.99% or higher was collected.

EXAMPLE 6

In 5 ml of a 1 N hydrochloric acid aqueous solution was dissolved 4.64 mmol of L-3-(2-naphthyl)-alanine having an optical purity of 96.0%, and the solution was neutralized at 30° C. with a 20% NaOH aqueous solution for crystallization. The precipitated crystals were worked-up in the same manner as in Example 2 to obtain 1.87 mmol of L-3-(2-naphthyl)-alanine having an optical purity of 99.99% or higher.

EXAMPLE 7

The same procedure of Example 2 was repeated, except that 10 mmol of D-phenylalaninol having an optical purity of 92.0% and 1.0 g of NaCl were dissolved in 5 ml of pure water at 30° C. and allowed to stand at 0 to 2° C. for crystallization. There was obtained 7.1 mmol of D-phenylalaninol having an optical purity of 99.99% or higher.

Process (B):

EXAMPLE 8

An aqueous solution (1100 g) containing 501.6 mmol of D-phenylalanine, 14.1 mmol - of L-phenylalanine (D/L ratio=97.2/2.8), and 1727 mmol of HCl was neutralized to a pH of about 5.5 at 30° C. with a 20% NaOH aqueous solution for crystallization. After cooling to room temperature, the crystals were collected by filtration by suction to recover 330.4 mmol of D-phenylalanine crystals having an optical purity of 99.2% as measured by HPLC (column: TSKgel Enantio L1, 4.6 mm (ID)×25 cm, produced by Tosoh Corp.).

The residual mother liquor weighing 1359 g which contained 185.6 mmol of D-phenylalanine having an optical purity of 93.6% was adjusted to pH 0.5 with concentrated hydrochloric acid, and the resulting solution was concentrated until crystals began to precipitate to carry out crystallization. The aqueous slurry containing the crystals was filtered by suction at room temperature to give 74.8 mmol of glossy and grayish crystals of D-phenylalanine hydrochloride having an optical purity of 99.2%. The mother liquor contained 110.8 mmol of D-phenylalanine having an optical purity of 89.7%.

EXAMPLE 9

The mother liquor recovered in Example 8, which contained 110.8 mmol of D-phenylalanine having an optical purity of 89.7%, was neutralized to a pH of about 5.5 at 30° C. with a 20% NaOH aqueous solution for crystallization. The precipitated crystals were collected by filtration to obtain 55.2 mmol of D-phenylalanine having an optical purity of 86.2%. The residual mother liquor contained 55.6 mmol of D-phenylalanine having an optical purity of 93.2%.

EXAMPLE 10

The D-phenylalanine hydrochloride having an optical purity of 99.2% which was obtained in Example 8 (74.8 mmol) was dissolved in 70 ml of pure water at 30° C., and the solution was neutralized to a pH of about 5.5 with a 20% NaOH aqueous solution for crystallization. The slurry containing the precipitated crystals was cooled to room temperature, followed by filtration by suction to give 61.4 mmol of D-phenylalanine having an optical purity of 99.9%.

EXAMPLE 11

An aqueous solution (1359 g) containing 185.6 mmol of D-phenylalanine having an optical purity of 93.6% was adjusted to pH 0.5 with concentrated hydrochloric acid, and the resulting solution was concentrated until crystals began to precipitate to carry out crystallization. The aqueous slurry of the precipitated crystals was filtered by suction at room temperature to give 74.8 mmol of glossy grayish crystals of D-phenylalanine hydrochloride having an optical purity of 99.2%. The mother liquor contained 110.8 mmol of D-phenylalanine having an optical purity of 89.7%.

The mother liquor was neutralized to a pH of about 5.5 with a 20% NaOH aqueous solution at 30° C. for crystallization. The precipitated crystals were collected by filtration to obtain 55.2 mmol of D-phenylalanine having an optical purity of 86.2%. The residual mother liquor contained 55.6 mmol of D-phenylalanine having an optical purity of 93.2%.

The mother liquor was adjusted to pH 0.5 with concentrated hydrochloric acid, and the resulting solution was concentrated until crystals began to precipitate to carry out crystallization. The aqueous slurry of the precipitated crystals was filtered by suction at room temperature to collect 22.4 mmol of D-phenylalanine hydrochloride having an optical purity of 99.2% (as measured by HPLC) as glossy and grayish crystals.

Process (C):

EXAMPLE 12

A hydrochloric acid aqueous solution containing 75 mmol of DL-phenylalanine, 36.4 mmol of L-phenylalanine methyl ester, and 223.0 mmol of D-phenylalanine methyl ester and an NaOH aqueous solution containing 190.9 mmol of N-benzyloxycarbonyl-L-aspartyl-L-phenylalanine methyl ester were mixed at 40° C., and the mixture was adjusted to pH 7 to form an adduct. To the aqueous slurry of the adduct was added 400 g of methyl isobutyl ketone to extract the adduct. The aqueous phase was separated, and the methyl isobutyl ketone phase was washed successively with 180 ml of pure water and three 180 ml portions of an aqueous solution containing 37.5 mmol of HCl to purity the adduct. An aqueous solution (180 g) containing 131.8 mmol of HCl was added thereto to acid-decompose the adduct at 50° C. The acidic aqueous phase was separated, and the solute was analyzed by liquid chromatography (column: TSKgel Enantio L1, 4.6 mm (ID)×25 cm, produced by Tosoh Corp.). As a result, the solution was found to contain 99.2 mmol of D-phenylalanine methyl ester, 0.8 mmol of L-phenylalanine methyl ester, and 0.6 mmol of DL-phenylalanine.

COMPARATIVE EXAMPLE 2

The same procedure as in Example 12 was repeated, except that 400 ml of an aqueous solution containing 375 mmol of HCl was added to the methyl isobutyl ketone phase (slurry) containing the adduct, that is, the adduct was directly subjected to acid decomposition without being washed with water nor an acidic solution. As a result of analysis, the separated acidic aqueous solution was found to contain 211.2 mmol of D-phenylalanine methyl ester, 29.2 mmol of L-phenylalanine methyl ester, and 28.0 mmol of DL-phenylalanine. That is, D-phenylalanine having sufficient chemical purity and optical purity were not recovered.

COMPARATIVE EXAMPLE 3

The same procedure as in Example 12 was repeated, except that the methyl isobutyl ketone phase (slurry) containing the adduct was washed with five 180 ml portions of pure water and then acid decomposed without being washed with an acidic solution. As a result of analysis, the separated acidic aqueous solution was found to contain 199.9 mmol of D-phenylalanine methyl ester, 15.6 mmol of L-phenylalanine methyl ester, and 3.6 mmol of DL-phenylalanine. That is, D-phenylalanine having sufficient chemical purity and optical purity were not recovered.

EXAMPLE 13

The same procedure as in Example 12 was repeated, except that the methyl isobutyl ketone phase (slurry) containing the adduct was washed successively with 180 ml of pure water and two 180 ml portions of a hydrochloric acid aqueous solution (HCl:60 mmol) and then acid decomposed. As a result of analysis, the separated acidic aqueous solution was found to contain 89.4 mmol of D-phenylalanine methyl ester, 1.1 mmol of L-phenylalanine methyl ester, and 0.5 mmol of DL-phenylalanine.

EXAMPLE 14

The same procedure as in Example 12 was repeated, except that the methyl isobutyl ketone phase (slurry) containing the adduct was washed successively with 180 ml of pure water, two 180 ml portions of a hydrochloric acid aqueous solution (HCl:20 mmol), and two 180 ml portions of pure water to purify the adduct slurry, and then the adduct was acid decomposed with 400 ml of a hydrochloric acid aqueous solution (HCl:335 mmol). As a result of analysis, the separated acidic aqueous solution was found to contain 153.4 mmol of D-phenylalanine methyl ester, 4.6 mmol of L-phenylalanine methyl ester, and 1.1 mmol of DL-phenylalanine.

EXAMPLE 15

The same procedure as in Example 12 was repeated, except that 250 mmol of DL-phenylalanine methyl ester, 25 mmol of DL-phenylalanine, and 125 mmol of N-benzyloxycarbonyl-L-aspartyl-L-phenylalanine methyl ester were reacted in an aqueous solution to form an adduct. As a result of analysis, the separated acidic aqueous solution was found to contain 41.6 mmol of D-phenylalanine methyl ester, 0.2 mmol of L-phenylalanine methyl ester, and 0.2 mmol of DL-phenylalanine.

While the invention has been described in detail and with reference to specific examples thereof, it will be apparent to one skilled in the art that various changes and modifications can be made therein without departing from the spirit and scope thereof.

This application is based on application Nos. Hei 8-256153, 8-256154 and 8-256155 filed in Japan, the entire content of which is incorporated hereinto by reference.

What is claimed is:

1. A method for purifying an optically active derivative of a D-amino acid from a preparation containing said optically active derivative and an optical isomer thereof, wherein said method comprises the steps of:

(1) reacting said preparation with an N-substituted-α-L-aspartyl-L-phenylalanine alkyl ester represented by the following formula (I):

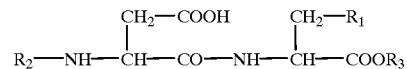

wherein $R_1$ represents a substituted or unsubstituted phenyl group; $R_2$ represents an aliphatic oxycarbonyl group or a substituted or unsubstituted benzyloxycarbonyl group; and $R_3$ represents an alkyl group, by mixing in an aqueous solution to form an adduct of the N-substituted-α-L-aspartyl-L-phenylalanine alkyl ester and the D-amino acid ester, so as to result in the formation of an adduct of said N-substituted alkyl ester;

(2) extracting said resulting adduct with a water-immiscible organic solvent to separate said adduct in the form of an organic solvent slurry from an aqueous phase, (3) purifying said organic solvent slurry containing the adduct by washing with an acid aqueous solution, and (4) subjecting said organic solvent slurry to acid decomposition with an aqueous acid solution to recover said optically active D-amino acid ester having a high optical purity as an acidic aqueous solution.

2. The method according to claim 1, wherein the acid of steps (3) and (4) is an organic or inorganic Brønsted acid.

3. The method according to claim 1, wherein the acid of step (3) is 0.1 to 0.7 mol per mole of said amino acid ester.

4. The method according to claim 1, wherein said washing with an acid aqueous solution of step (3) is carried out by using the acid aqueous solution at least 2 times.

5. The method according to claim 1, wherein the water-immiscible organic solvent of step (2) is methyl isobutyl ketone or isobutyl acetate.

6. The method of claim 1, wherein said recovered optically active amino acid or derivative thereof has a high optical purity.

7. The method of claim 1, wherein said derivative of said optically active amino acid is a hydrochloride.

8. The method of claim 1, wherein said optically active amino acid or derivative thereof is at least one selected from the group consisting of phenylglycine and derivatives thereof, phenylalanine and derivatives thereof, homophenylalanine and derivatives thereof, and naphthylalanine and derivatives thereof.

9. A method for purifying an optically active D-amino acid or derivative thereof from a preparation containing said optically active amino acid or derivative and an optical isomer thereof, wherein said method comprises the steps of:

(1) adjusting the pH of said preparation to approximately the isoelectric point of said optically active amino acid or derivative thereof thereby causing said optically active amino acid or derivative thereof to crystallize from a mother liquor;

(2) collecting said crystallized optically active amino acid or derivative thereof;

(3) lowering the pH of said mother liquor from which said crystals have been collected to a pH of 1 or less, followed by crystallization.

10. The method according to claim 9, wherein said process additionally comprises the steps:

(4) subjecting the mother liquor from which the crystals have been collected to crystallization by neutralization at about the isoelectric point to recover the mother liquor as a solution of an optically active amino acid whose optical purity corresponds to a convergent value of mutual solubility of the optical isomers, and (5) lowering the pH of the mother liquor to 1 or less and subjecting the mother liquor to crystallization at a prescribed concentration.

11. The method of claim 9, wherein said recovered optically active amino acid or derivative thereof has a high optical purity.

12. The method of claim 9, wherein said derivative of said optically active amino acid is a hydrochloride.

13. The method of claim 9, wherein said optically active amino acid or derivative thereof is at least one selected from the group consisting of phenylglycine and derivatives thereof, phenylalanine and derivatives thereof, homophenylalanine and derivatives thereof, and naphthylalanine and derivatives thereof.

14. A method for purifying an optically active D-amino acid or derivative thereof from a preparation containing said optically active amino acid or derivative and an optical isomer thereof, wherein said optically active amino acid or derivative thereof is in excess relative to the concentration of said optical isomer, wherein said method comprises the steps of:

(1) adjusting the concentration of said optically active amino acid or derivative thereof such that it has an optical purity that is higher than a convergent value of a mutual solubility of said optical isomers, and (2) crystallizing by neutralization said optically active amino acid or derivative thereof that exists in excess.

15. The method of claim 14, wherein said recovered optically active amino acid or derivative thereof has a high optical purity.

16. The method of claim 14, wherein said derivative of said optically active amino acid is a hydrochloride.

17. The method of claim 14, wherein said optically active amino acid or derivative thereof is at least one selected from the group consisting of phenylglycine and derivatives thereof, phenylalanine and derivatives thereof, homophenylalanine and derivatives thereof, and naphthylalanine and derivatives thereof.

* * * * *

UNITED STATES PATENT AND TRADEMARK OFFICE
CERTIFICATE OF CORRECTION

PATENT NO : 6,008,403
DATED : December 28, 1999
INVENTOR(S): Kimio Katsuura, Shigeaki Irino and Akira Tokuda It is certified that error appears in the above-identified patent and that said Letters Patent are hereby corrected as shown below:

On the title page, item 54 (Title)
    Replace the word "of" by the word -- or --.
In column 1, line 2,
    Replace the word "of" by the word -- or --.

Signed and Sealed this

Twenty-seventh Day of June, 2000

Q. TODD DICKINSON

*Attest:*

*Attesting Officer*      *Director of Patents and Trademarks*